United States Patent [19]

Fujimoto et al.

[11] 4,247,706
[45] Jan. 27, 1981

[54] DIBENZOTHIEPIN DERIVATIVES AND A PROCESS FOR PRODUCING THE SAME

[75] Inventors: Yasuo Fujimoto, Tokyo; Shigeru Yamabe, Kobe, both of Japan

[73] Assignee: Nippon Chemiphar Co., Ltd., Tokyo, Japan

[21] Appl. No.: 84,163

[22] Filed: Oct. 12, 1979

[30] Foreign Application Priority Data

Oct. 17, 1978 [JP] Japan .................... 53-126846

[51] Int. Cl.³ .................................. C07D 337/14
[52] U.S. Cl. ........................ 549/12; 424/275; 560/9; 260/465 D
[58] Field of Search ........................................ 549/12

[56] References Cited

U.S. PATENT DOCUMENTS

| | | | |
|---|---|---|---|
| 4,101,667 | 7/1978 | Yamabe et al. | 424/275 OR |
| 4,104,280 | 8/1978 | Ackrell | 549/12 OR |

OTHER PUBLICATIONS

Degering, An Outline of Organic Chemistry, 6th Ed., pp. 64 and 137–138, Barnes and Noble, Inc. (1951) (NY).

Primary Examiner—John D. Randolph
Attorney, Agent, or Firm—Oblon, Fisher, Spivak, McClelland & Maier

[57] ABSTRACT

A compound of the formula,

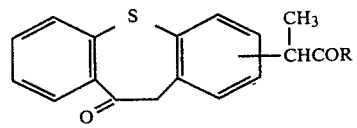

wherein R represents a hydroxy or amino group is an antiinflammatory and analgesic agent.

3 Claims, No Drawings

DIBENZOTHIEPIN DERIVATIVES AND A PROCESS FOR PRODUCING THE SAME

BACKGROUND OF THE INVENTION

This invention relates to novel dibenzothiepin derivatives and to a process for producing the same.

The present inventors have studied a wide variety of thiepin derivatives, and as a result, they have found that dibenzothiepin derivatives of the formula (I),

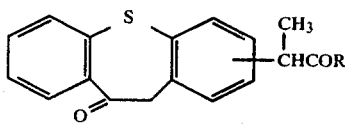

wherein R represents a hydroxy or amino group, possess excellent antiinflammatory and analgesic activities. A novel process for producing the dibenzothiepin derivatives has also been found.

SUMMARY OF THE INVENTION

It is, therefore, one object of this invention to provide novel dibenzothiepin derivatives having the formula (I) and exhibiting strong antiinflammatory and analgesic action.

It is another object of the invention to provide a novel process for producing the dibenzothiepin derivatives of the formula (I).

DETAILED DESCRIPTION OF THE PREFERRED EMBODIMENTS

Compounds of the formula (I) are divided into the following groups of the formulae (II) and (III).

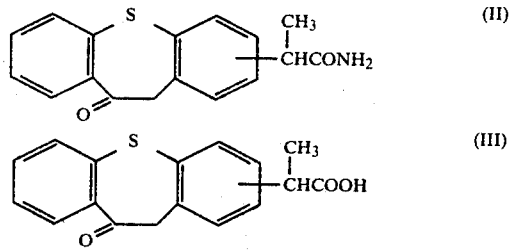

Of the above groups, particularly preferable is a compound having the formula (III).

According to the present invention, the compounds of the formula (I) can be produced by the process as hereinafter advanced.

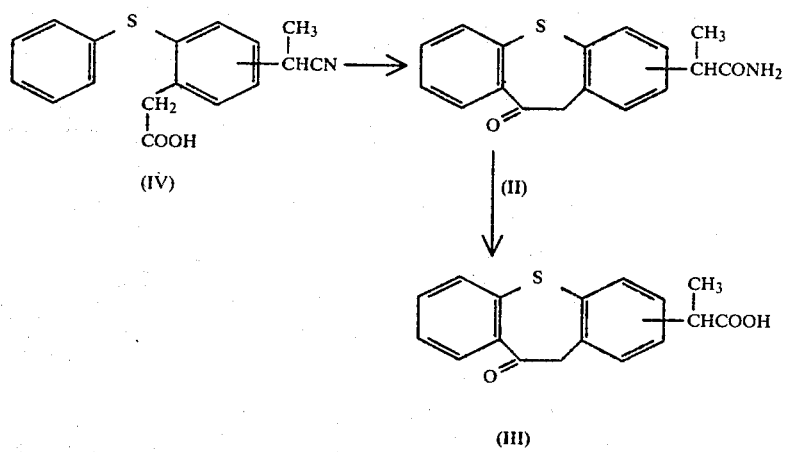

That is, a compound of the formula (II) is produced by cyclizing a compound of the formula (IV) or an active derivative thereof in the presence of a condensing agent. Suitable condensing agents which are useful in the invention include, for example, polyphosphoric acid, polyphosphoric acid ester and the like. The reaction is preferably conducted for 0.5 to 3 hours at 70° to 200° C. with or without a solvent such as benzene, toluene or xylene.

The compound of the formula (III) is produced by hydrolyzing the compound of the formula (II). The reaction is carried out by any usual method, that is, with the use of water or a solvent containing a small amount of water, for example, an alcohol such as methanol or ethanol, in the presence of a catalyst such as potassium hydroxide, sodium hydroxide, hydrochloric acid or sulfuric acid at temperatures from room temperature to the boiling point of the solvent for 3 to 10 hours.

The starting material of the formula (IV) is produced by the following reaction scheme.

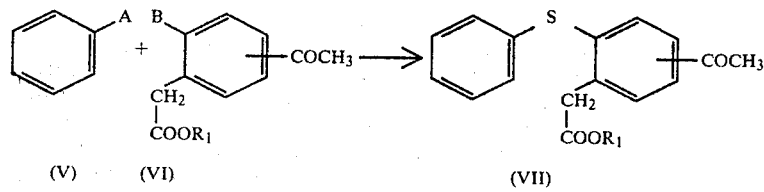

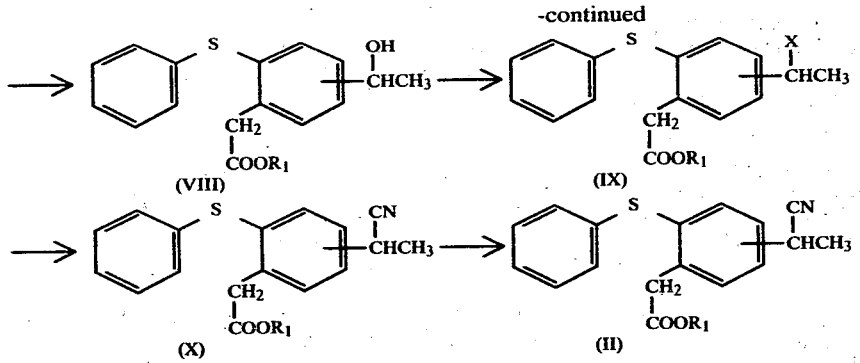

wherein A and B each represent a halogen atom, a mercapto group or a metallic salt thereof in which A is a halogen atom when B is a mercapto group or a metallic salt thereof, and A is a mercapto group or a metallic salt thereof when B is a halogen atom, $R_1$ represents an ester residue, and X represents a halogen atom.

A compound of the formula (V) is reacted with a compound of the formula (VI) to produce a compound of the formula (VII), which is reduced to produce a compound of the formula (VIII), which is halogenated to produce a compound of the formula (IX), which is reacted with a metallic cyanide to produce a compound of the formula (X), which is hydrolyzed, whereby the compound of the formula (II) is obtained.

The compound of the formula (I) according to the present invention possesses excellent antiinflammatory and analgesic effects, as is demonstrated by the following experiments.

(1) Antiinflammatory Effect

Male Wister rats each weighing about 100 g, one group consisting of 5 to 7 rats, were orally given test compounds, and edema was then induced in the hind paws by a subcutaneous injection of 0.1 ml of a 1% carrageenan saline solution one hour after the administration of the test compounds. With a predetermined lapse of time, the volumes of the hind paws were measured by a volume differential meter. Indomethacin was used as an active placebo. The results obtained are shown in Table 1.

TABLE 1

| Test compounds | Dosage (mg/kg) | Inhibition (%) (after 3 hours) |
|---|---|---|
| Compound 1 | 2 | 52.5 |
| Compound 2 | 2 | 55.8 |
|  | 2 | 35.9 |
| Indomethacin | 4 | 51.9 |

Compound 1: 2-(10,11-Dihydro-10-oxodibenzo[b,f]thiepin-2-yl)propionamide
Compound 2: 2-(10,11-Dihydro-10-oxodibenzo[b,f]thiepin-2-yl)propionic acid (2) Analgesic Effect dd Male mice each weighing 18 to 22 g, one group consisting of 10 mice, were given by an intraperitoneal injection of 0.6% acetic acid in a dosage of 0.1 ml/10 g/body weight. The number of writhing syndromes occurring within 20 minutes after the injection was observed. These animals were given orally test compounds suspended in a 0.2% carboxymethylcellulose solution 30 minutes before the injection of acetic acid. The inhibitory percentage of each of the test compounds was calculated in comparison with a control in which a 0.2% carboxymethylcellulose solution only was given. Aspirin was used as an active placebo. Two prior art compounds disclosed in U.S. Pat. No. 4,104,280 were used for purposes of comparison. The results obtained are shown in Table 2 in terms of the ratio to Aspirin together with the antiinflammatory activity in terms of the ratio to Indomethacin.

TABLE 2

| Test compounds | Antiinflammatory activity (ratio to Indomethacin) | Analgesic activity (ratio to Aspirin) |
|---|---|---|
| Compound 2 | 2 | 20 |
| Comparative compound A | 0.01 | 1 |
| Comparative compound B | 0.01 | 1 |
| Indomethacin | 1 | — |
| Aspirin | — | 1 |

Compound 2: Same as defined above.
Comparative compound A: (10,11-Dihydro-10-oxodibenzo[b,f]-thiepin-2-yl)-acetic acid (U.S. Pat. No. 4,104,280)
Comparative compound B: (10,11-Dihydro-10-oxodibenzo[b,f]-thiepin-3-yl)-acetic acid (U.S. Pat. No. 4,104,280)

As is clear from the results of Tables 1 and 2 above, the present compounds possess significant potency in comparison with the prior art compounds, and compound 2 which is typical of this invention has an $LD_{50}$ value of 232 mg/kg relative to the rats by the Lichfield-Wilcoxon method. This fact confirms the excellent effects of the present compounds.

The compounds of the present invention may be administered not only in the form of a free acid but also in the form of a non-toxic salt. Suitable non-toxic salts include sodium, potassium, calcium and aluminium salts.

The compounds of this invention exhibit both oral and parenteral activities and can be formulated in various dosage forms for oral, parenteral, rectal and topical administration. The solid dosage form for oral administration includes a capsule, tablet, pill, powder or granule. In the solid dosage form, the active compounds are admixed with at least one inert diluent such as sucrose, lactose or starch. Such dosage form may also comprise, as is in the normal practice, a substance other than the inert diluent, for example, a lubricating agent such as magnesium stearate. In the case where the compounds are used in the form of a capsule, tablet or pill, a buffering agent can be further employed. The tablet and pill can additionally be prepared with an enteric coating.

The liquid dosage form for oral administration includes a pharmaceutically acceptable emulsion, solution, suspension, syrup or elixir containing an inert diluent commonly used in the art such as purified water or an alcohol. In addition to the inert diluent, compositions including adjuvants such as a wetting agent, emulsifying and suspending agent, and sweetening, flavoring and perfuming agent may be utilized in the practice of this invention. The preparation for parenteral administration according to the invention includes a sterile aqueous or non-aqueous solution, suspension or emulsion. Examples of the non-aqueous solvent or vehicle are propylene glycol, polyethylene glycol, vegetable oils such as olive oil, and injectable organic esters such as ethyl oleate. The composition for rectal administration is a suppository which may contain, besides the active ingredients, an excipient such as cocoa butter or a suppository wax.

The dosages of the compounds of this invention in various compositions actually utilized may be varied. However, it is necessary that the amount of the compounds be such that any one suitable dosage form is attained. Any selected dosage depends upon the desired therapeutic effect, administration route and treatment duration. Such dosage lies, in general, in a range from 0.4 to 20 mg/kg of body weight.

This invention is illustrated in further detail with reference to certain specific Examples, but the invention is not limited to these Examples.

EXAMPLE 1

2-(10,11-Dihydro-10-oxodibenzo[b,f]thiepin-2-yl)-propionamide:

To 1.20 g of 3-(α-cyanoethyl)-6-phenylthiophenyl acetic acid was added 25 g of polyphosphoric acid, and the mixture was stirred at 120° C. for 15 minutes. To the resulting mixture was added ice water, and the mixture was extracted with ethyl acetate. The extract was washed with a saturated sodium chloride solution and dried over anhydrous sodium sulfate. The solvent was removed by distillation to obtain a yellowish brown oil substance, which was chromatographed over 30 g of silica gel and eluted with chloroform to obtain light brown crystals. The crystals were recrystallized from acetone-n-hexane. Thereby obtaining 0.33 g (yield: 28%) of 2-(10,11-dihydro-10-oxodibenzo[b,f]thiepin-2-yl)-propionamide as light yellow crystals having a melting point of 184°–185.5° C.

| IR $\nu_{max}^{KBr}$ cm$^{-1}$: | 3340, 3180 (NH$_2$), 1660 (C=O) |
|---|---|
| | 1.34 (3H, d, J = 7Hz, =CHCH$_3$) |
| NMR $\begin{pmatrix}DMSO-d_6\\acetone-d_6\end{pmatrix}\delta$: | |
| | 3.66 (1H, q, J = 7Hz, =CHCH$_3$) |
| | 4.28 (2H, s, —CH$_2$CO—) |
| | 6.55 (1H, b.s, =NH) |
| | 7.06–7.78 (7H, m, aromatic protons and =NH) |
| | 8.05 (1H, dd, J = 8, 2Hz, C$_9$—H) |
| MS m/e: | 297 (M$^+$) |

EXAMPLE 2

2-(10,11-Dihydro-10-oxodibenzo[b,f]thiepin-2-yl)-propionic acid:

To a mixture of 150 mg of 2-(10,11-dihydro-10-oxodibenzo[b,f]-thiepin-2-yl)-propionamide and 2 ml of ethanol was added 400 mg of potassium hydroxide in 2 ml of water, and the mixture was refluxed with stirring for 6 hours. After the completion of the reaction, ethanol was removed by distillation to obtain a residue to which was added water. The residue was washed with ethyl acetate, and an alkaline layer was acidified with hydrochloric acid and extracted with ethyl acetate. The extract was washed with a saturated sodium chloride solution and dried over anhydrous sodium sulfate. The solvent was removed by distillation to obtain a brown oil substance, which was chromatographed over 4 g of silica gel and eluted with benzene-chloroform (1:1) to obtain a light yellow oil substance. This substance was recrystallized from benzene-n-hexane, thereby obtaining 96 mg (yield: 64%) of 2-(10,11-dihydro-10-oxodibenzo[b,f]thiepin-2-yl)-propionic acid as pale yellow crystals having a melting point of 130.5°–131.5° C.

| IR $\nu_{max}^{KBr}$ cm$^{-1}$: | 1710, 1675 (C=O) |
|---|---|
| NMR (CDCl$_3$)$\delta$: | 1.46 (3H, d, J = 7Hz, =CHCH$_3$) |
| | 3.68 (1H, q, J = 7Hz, =CHCH$_3$) |
| | 4.29 (2H, s, —CH$_2$CO—) |
| | 6.92–7.64 (6H, m, aromatic protons) |
| | 8.07 (1H, dd, J = 8, 2Hz, C$_9$—H) |
| | 10.02 (1H, b.s, —COOH) |
| MS m/e: | 298 (M$^+$) |

What is claimed is:

1. A compound of the formula,

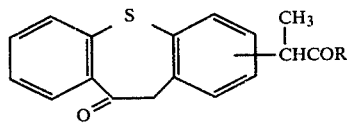

wherein R represents a hydroxy or amino group.

2. 2-(10,11-Dihydro-10-oxodibenzo[b,f]thiepin-2-yl)-propionic acid.

3. 2-(10,11-Dihydro-10-oxodibenzo[b,f]thiepin-2-yl)-propionamide.

* * * * *